(12) United States Patent
Greenstein

(10) Patent No.: US 7,902,350 B2
(45) Date of Patent: Mar. 8, 2011

(54) **METHOD FOR MONITORING THE EFFICACY OF A *MYCOBACTERIUM AVIUM* SUBSPECIES *PARATUBERCULOSIS* THERAPY**

(76) Inventor: Robert J. Greenstein, Tenafly, NJ (US)

( * ) Notice: Subject to any disclaimer, the term of this patent is extended or adjusted under 35 U.S.C. 154(b) by 267 days.

(21) Appl. No.: 12/255,940

(22) Filed: Oct. 22, 2008

(65) Prior Publication Data

US 2009/0111116 A1    Apr. 30, 2009

Related U.S. Application Data

(60) Provisional application No. 60/982,527, filed on Oct. 25, 2007.

(51) Int. Cl.
*C07H 21/04* (2006.01)
*C00H 21/02* (2006.01)
*A61K 39/04* (2006.01)

(52) U.S. Cl. ......... 536/23.7; 536/23.1; 424/9.1; 424/9.2; 424/248.1

(58) Field of Classification Search ................. 536/23.1, 536/23.7; 424/9.1, 9.2, 248
See application file for complete search history.

(56) References Cited

U.S. PATENT DOCUMENTS

2003/0175725 A1 * 9/2003 Kapur et al. ............. 435/6
2003/0228642 A1 * 12/2003 Shafran ................... 435/7.32

OTHER PUBLICATIONS

Greenstein et al., "On the action of methotrexate and 6-mercaptopurine on *M. avium* subspecies *paratuberculosis*", PloS ONE 2007 2(1):e161 pp. 1-5.
Greenstein et al., "On the action of 5-amino-salicylic acid and sulfapyridine on *M. avium* including subspecies *paratuberculosis*", PloS ONE 2007 6:e516 pp. 1-5.
Mishina et al., "On the etiology of Crohn disease", Proc. Natl. Acad. Sci. USA 1996 93:9816-9820.
Millar et al., "IS900 PCR to detect *Mycobacterium paratuberculosis* in retail supplies of whole pasteurized cows' milk in England and Wales", Applied and Environmental Microbiology 1996 62(9):3446-3452.

* cited by examiner

*Primary Examiner* — Rodney P. Swartz
(74) *Attorney, Agent, or Firm* — Licata & Tyrrell P.C.

(57) ABSTRACT

The present invention relates to *Mycobacterium avium* subspecies paratuberculosis (MAP) as the etiological agent of IBD, including ulcerative colitis and Crohn's disease, as well as Multiple Sclerosis and Alzheimer's Disease. As such, methods for monitoring efficacy of a anti-MAP therapy and determining whether a blood sample is suitable for transfusion are provided based upon presence, absence or amount of MAP nucleic acid.

1 Claim, 6 Drawing Sheets

METHOD FOR MONITORING THE EFFICACY OF A *MYCOBACTERIUM AVIUM* SUBSPECIES *PARATUBERCULOSIS* THERAPY

This application claims the benefit of U.S. Provisional Application No. 60/982,527, filed Oct. 25, 2007, which is herein incorporated by reference in its entirety.

BACKGROUND OF THE INVENTION

Johne's disease is a chronic diarrheal enteric disease in ruminants that is caused by *Mycobacterium avium* subspecies paratuberculosis (MAP) (Johne & Frothingham (1895) *Dtsch. Zeitschr. Tiermed. Vergl. Pathol.* 21:438-454). Live MAP is shed into the milk of cows with Johne's disease (Sweeney (1996) *Vet. Clin. North Am. Food Anim. Pract.* 12(2):305-12). MAP has been cultured from commercially available pasteurized milk in Europe and the United States (Grant (1998) *Appl. Environ. Microbiol.* 64(7):2760-1; Ellingson, et al. (2005) *J. Food Prot.* 68(5):966-72). When Crohn's disease was first described (Crohn, et al. (1932) *J. Amer. Med. Assoc.* 99:1323-1328), similarities to Johne's disease were identified (Dalziel (1913) *Br. Med. J.* ii:1068-1070). However, in humans MAP exists in the cell wall-deficient form (Chiodini (1987) *J. Clin. Microbiol.* 25:796-801). Therefore, in the early analysis of Crohn's disease, MAP could not be detected in humans by the mycobacterial identification techniques of the time, because such techniques stained the mycobacterial cell wall (Ziehl (1882) *Dtsch. Med. Wschr.* 8:451; Neelsen (1883) *Zbl. Med. Wiss.* 21:497-501). However, since 1913 the presence of MAP has been identified in humans by other means (see, e.g., Greenstein (2003) *Lancet Infect. Dis.* 3(8):507-14) and an infectious etiology has been posited for some (Hermon-Taylor (1998) Ital. *J. Gastroenterol. Hepatol.* 30(6):607-10; Borody, et al. (2002) *Dig. Liver Dis.* 34(1):29-38), or all (Greenstein (2005) Genetics, Barrier Function, Immunologic & Microbial Pathways. Munster, Germany: 25) of inflammatory bowel disease (IBD).

Since the first detection of MAP RNA (Mishina, et al. (1996) Proc. Natl. Acad. Sci. USA 93(18):9816-9820), MAP has been suggested as being the primary and unique, etiological agent of all IBD (Naser, et al. (2004) Lancet 364(9439): 1039-1044; Autschbach, et al. (2005) Gut 54(7):944-9; Greenstein (2005) supra; Greenstein (2005) Genetics, Barrier Function, Immunologic & Microbial Pathways. Munster, Germany: 24; Greenstein (2005) Crohn's and Colitis Foundation (CCFA) National Research and Clinical Conference. Fourth Annual Advances in Inflammatory Bowel Disease. Miami, Fla.:211) including perforating and non-perforating Crohn's disease (Greenstein, et al. (1988) GUT 29:588-592; Gilberts, et al. (1994) Proc. Natl. Acad. Sci. USA 91(126): 12721-12724) and ulcerative colitis. It is believed that the particular clinical presentation of IBD that manifests is dependent upon the infected individual's immune response to MAP (Gilberts, et al. (1994) supra). This is analogous to another mycobacterial disease, leprosy. There are two clinical forms of leprosy, tuberculoid and lepromatous (Hansen (1874) Norsk Magazin Laegevidenskaben 4:1-88), both of which are caused by the same organism, M. leprae. The form of leprosy that manifests in a given individual is determined by the immune response of the infected patient (Yamamura, et al. (1991) Science 254:277-279), not by the phenotype or genotype of the leprosy bacillus.

It has been suggested that Koch's postulates (Koch (1882) *Berl. Klin. Wschr.* 19:221-230), originally promulgated for use in demonstrating tuberculosis infection, may have been met for MAP in Crohn's disease (Greenstein (2003) supra) and more recently for MAP in ulcerative colitis (Greenstein (2005) supra; Naser, et al. (2004) supra).

The link between MAP infection and other diseases has not been as extensively analyzed. An association between ulcerative colitis and Multiple Sclerosis has been suggested (Rang, et al. (1982) *The Lancet* pg. 555) and the positive association between IBD incidence rates and Multiple Sclerosis has led to the suggestion that these two chronic, immunologically-mediated diseases may have a common environmental etiology (Green, et al. (2006) *Am. J. Epidemiol.* 164(7):615-23). However, the common causal agent of ulcerative colitis and Multiple Sclerosis was not identified. Moreover, while the symptoms of Multiple Sclerosis have been ameliorated with variety of therapeutic agents including azathioprine, methotrexate, cyclophosphamide and mitoxantrone (Kaffaroni, et al. (2006) *Neurol. Sci.* 27 Suppl. 1:S13-7), which have been suggested to mediate the secondary inflammatory response, there has been no indication that these agents affect the primary etiological agent.

SUMMARY OF THE INVENTION

The present invention is a method for monitoring efficacy of a anti-*Mycobacterium avium* subspecies paratuberculosis (MAP) therapy. The method involves determining the presence or amount of a MAP nucleic acid before and after treatment with an anti-MAP therapeutic agent, wherein the absence or a decrease in the amount of MAP nucleic acid is indicative of the efficacy of the anti-MAP therapeutic agent.

The present invention is also a method for determining whether a blood sample is suitable for transfusion by determining the presence of a *Mycobacterium avium* subspecies paratuberculosis (MAP) nucleic acid, wherein the presence of a MAP nucleic acid indicates that the blood sample is not suitable for transfusion.

BRIEF DESCRIPTION OF THE DRAWINGS

FIG. 1 shows the frequency of blood samples containing MAP DNA, as determined by PCR analysis. FIG. 1A shows the frequency of MAP DNA in healthy donors compared to patients with IBD. FIG. 1B shows the frequency of MAP DNA in IBD patients with active or inactive disease.

FIG. 2 shows the MAP DNA frequency as a function of the therapy being received. Frequency is presented as percent of total subjects analyzed.

FIG. 3 shows the interaction between anti-MAP and steroid treatment. MAP DNA frequency is presented as percent of total subjects analyzed.

DETAILED DESCRIPTION OF THE INVENTION

Analogous to lepromatous leprosy and tuberculoid leprosy, it is now posited that Multiple Sclerosis and perforating Crohn's disease are the "acute" forms of a *Mycobacterium avium* subspecies paratuberculosis (MAP) infection, whereas Alzheimer's Disease and obstructive Crohn's or ulcerative colitis are the chronic forms of a MAP infection. It is further posited that a causative relationship between MAP and diseases such as IBD and Multiple Sclerosis have been missed because it has not been appreciated that standard treatment regimes, whose mechanisms of actions are unknown or speculated upon, are in fact effective because they are treating a MAP infection. The panoply of medications that are used to treat diseases such as IBD and Multiple Sclerosis can be divided into two groups; one that treats a MAP infection and the other that treats the inflammatory condition that is consequent to the primary infection.

Indeed, it has now been found that there is a high prevalence of *Mycobacterium avium* subspecies paratuberculosis (MAP) DNA in the blood of healthy human blood donors and the effect of treatment with chronic anti-MAP antibiotic therapy in patients with Inflammatory Bowel Disease (IBD) results in the decreased prevalence of MAP DNA in the blood. Demonstration of in vitro activity of certain anti-IBD drugs (Greenstein, et al. (2007) *PLoS ONE* 2(1):e161; Greenstein, et al. (2007) *PLoS ONE* 2(6):e516), prompted the investigation of the association of treatment and bacteremia in a set of human samples, where microbiological and immunological variables had been studied. Accordingly, the blood of 100 healthy individuals and 246 patients with IBD (134 patents with Crohn's disease, 104 with ulcerative colitis and 8 with indeterminate colitis) was evaluated for MAP DNA using nested PCR. Geographically, the IBD patients were from the provinces of Alava (82 patients), Bizkaia (100 patients) or Gipuzkoa (65 patients). Statistical analysis was by the Fischer Exact Test or Pearson Correlation as necessary.

Figure 1A:
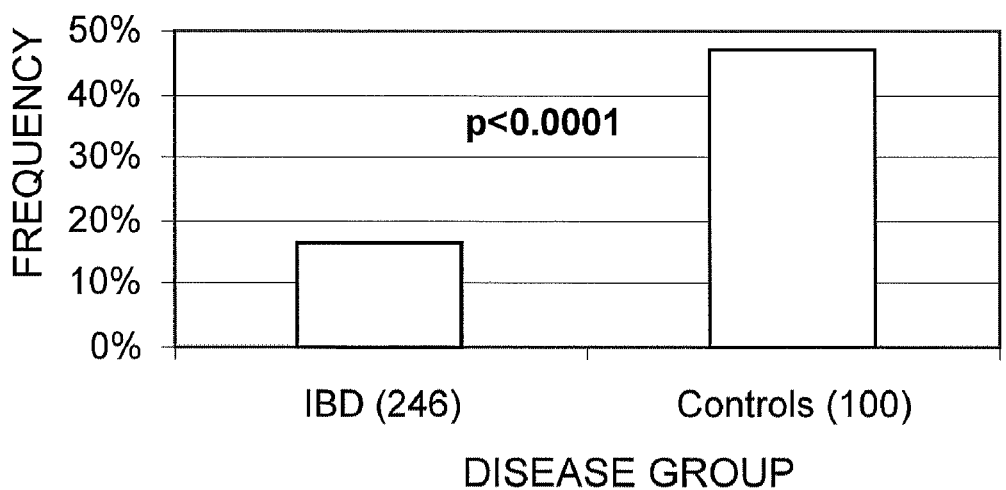
Figure 1B:
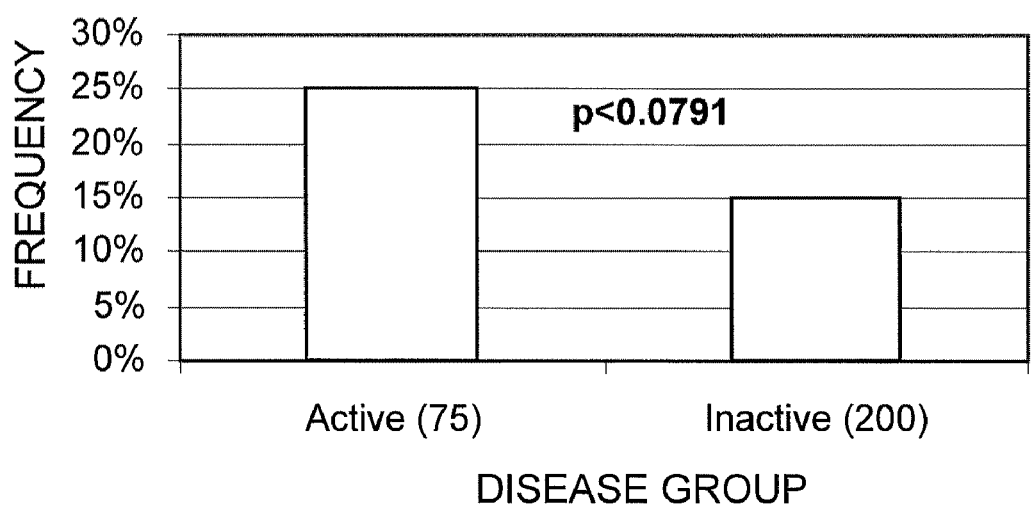
Figure 2:
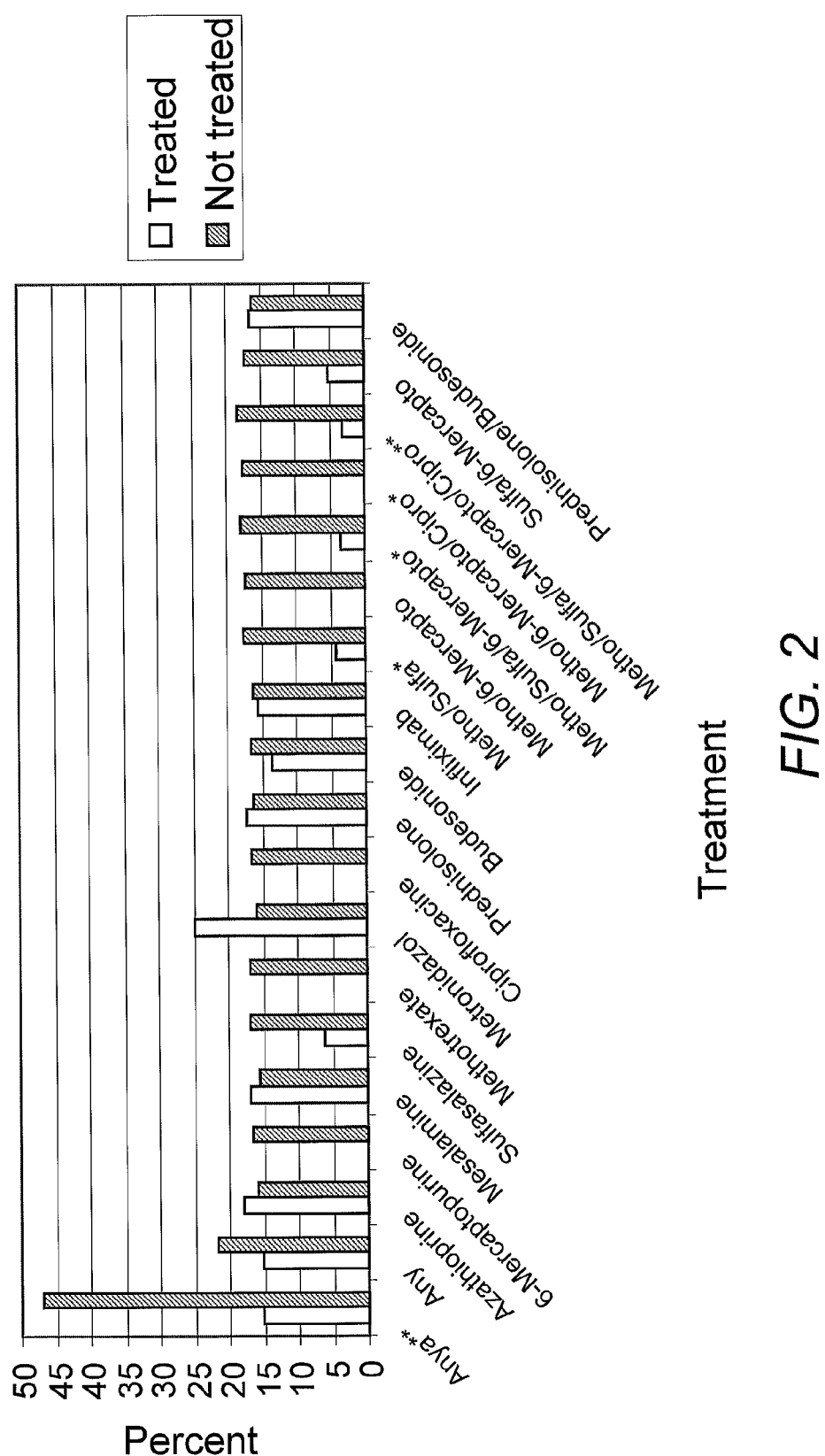
Figure 3:
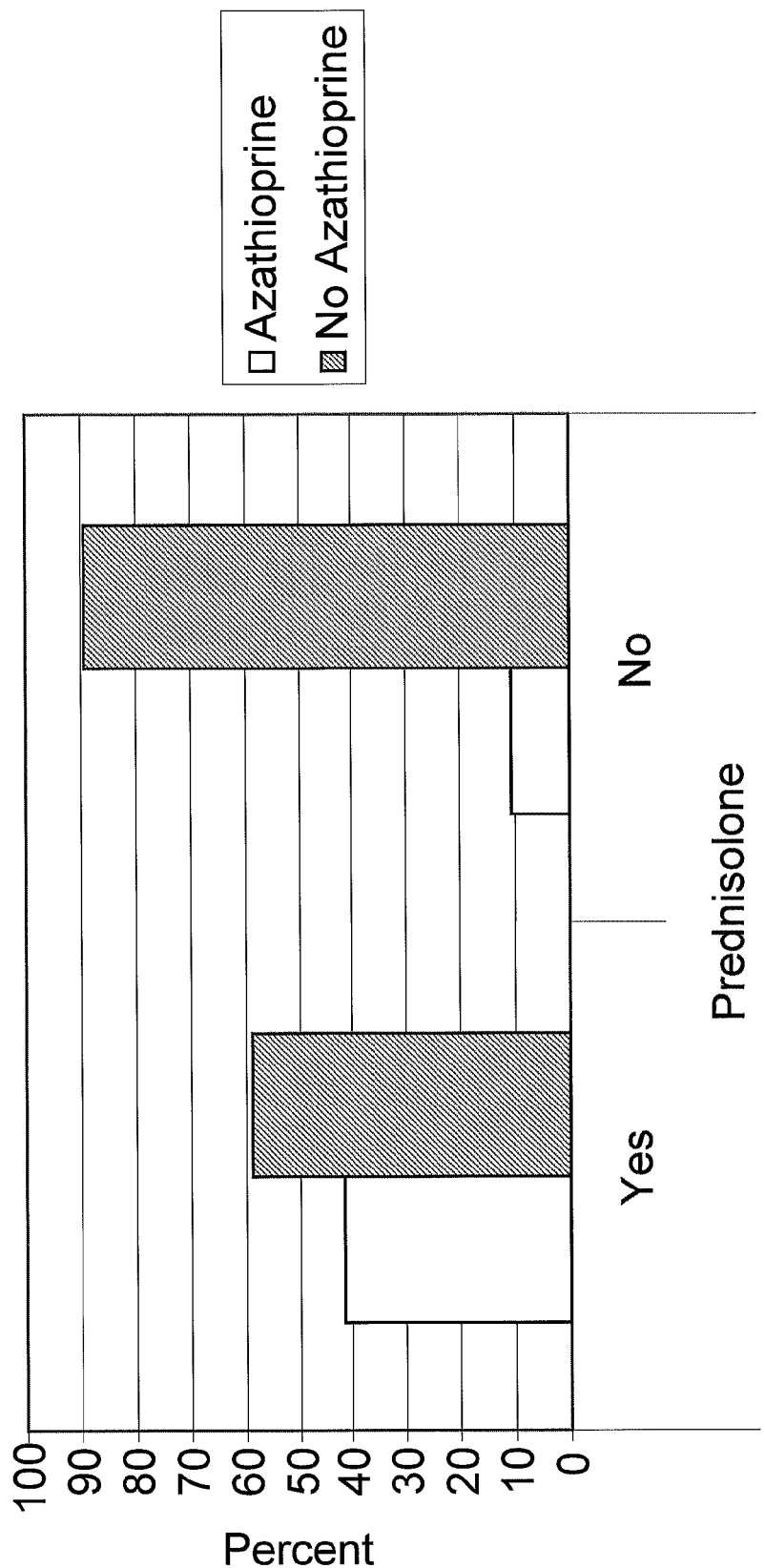
Figure 4:
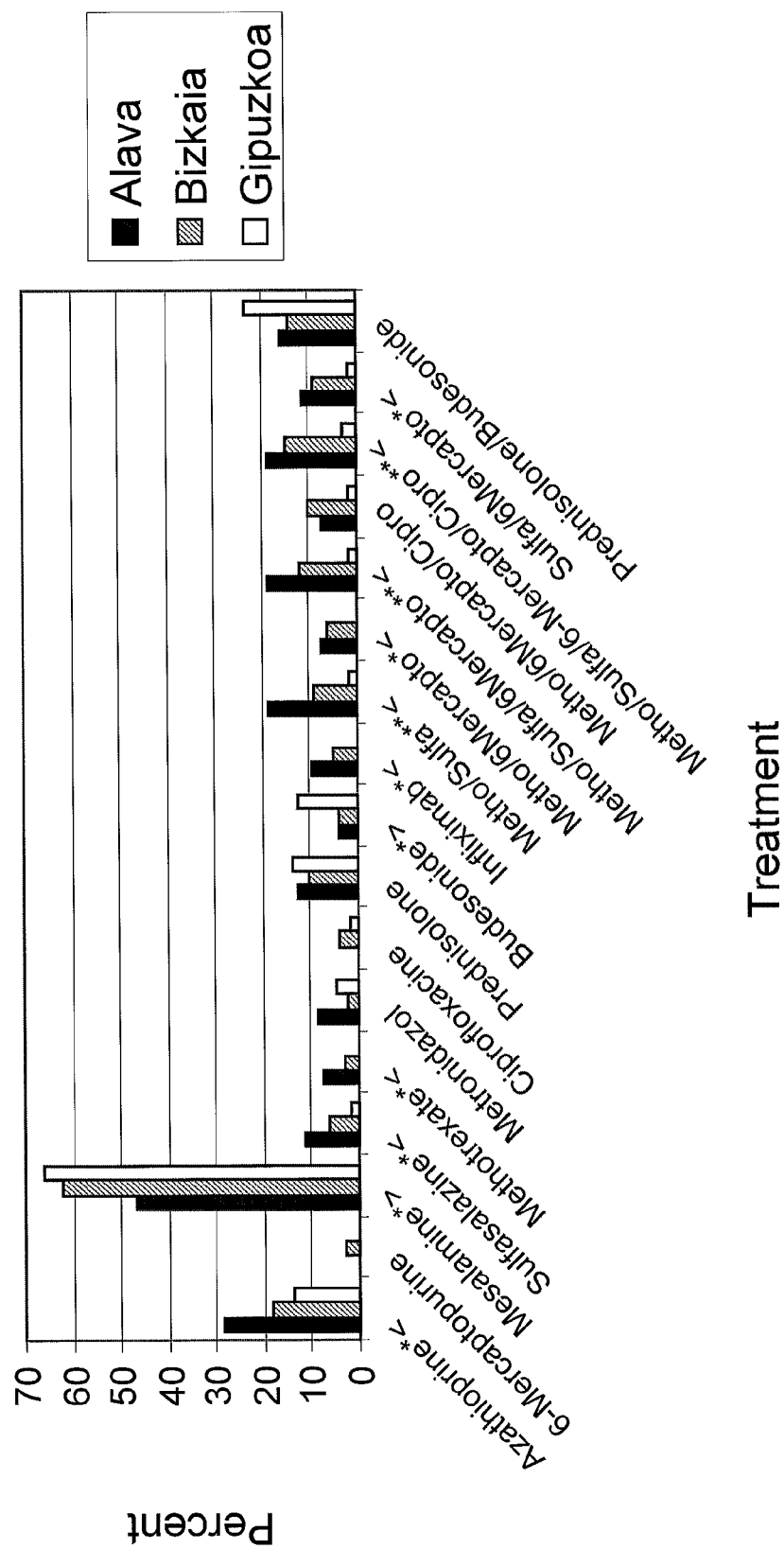
FIG. 4 shows MAP DNA prevalence base upon geographical location, disease activity, and pattern of treatment. MAP DNA prevalence is presented as percent of total subjects analyzed.
Figure 5A:
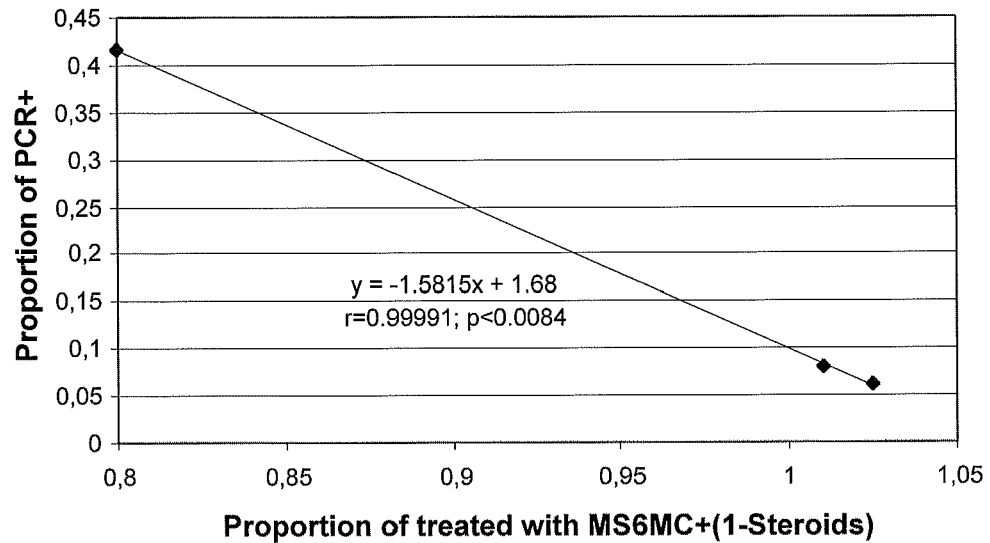
FIG. 5 shows the correlation of drug combination (MS6MC) treatment effects with (FIG. 5A) or without (FIG. 5B) steroid therapy and a comparison of the same (FIG. 5C).
Figure 5B:
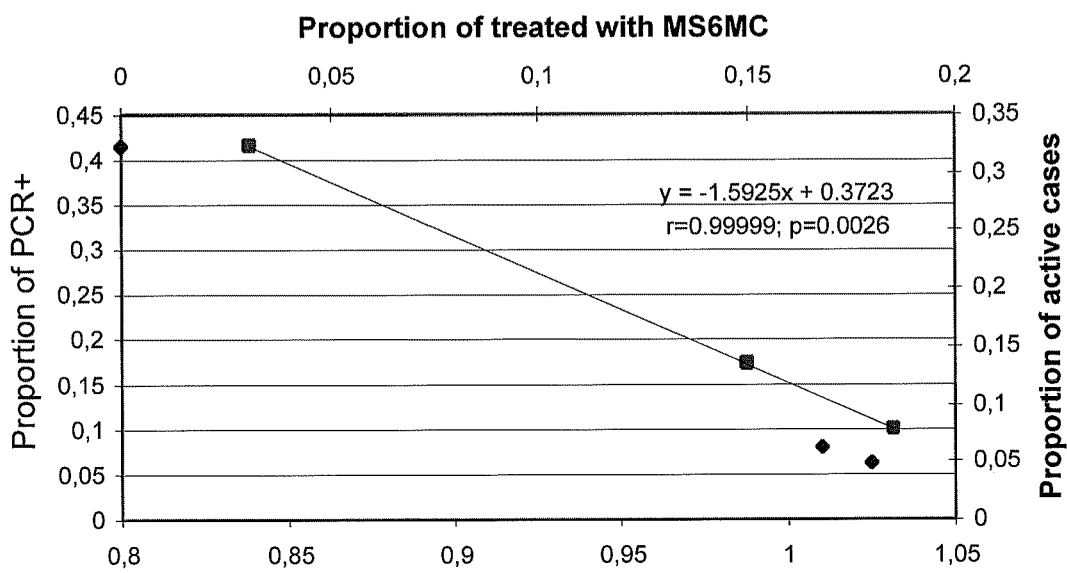
Figure 5C:
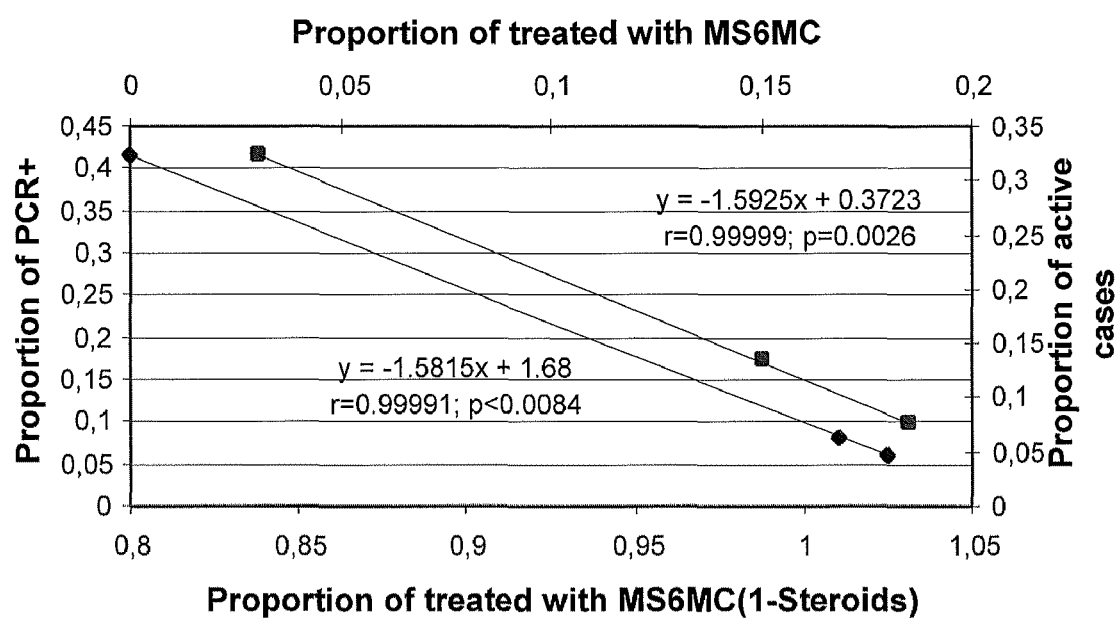

The results of this analysis indicated that MAP DNA was detected in 47% (47/100) of the healthy controls and in 16.3% (40/246) of all subjects with IBD ($p<0.0001$) (FIG. 1A). Furthermore, MAP DNA was found in 15% of IBD patients, who were receiving any anti-MAP antibiotic therapy and reported an inactive disease status (FIG. 1B). Moreover, when comparing the type of treatment being received, the lowest MAP DNA frequency was observed with patients who received a combination therapy of methotrexate, sulfasalazine, 6-Mercaptopurine or Ciprofloxacin 3.1% (1/32) ($p<0.02$) (FIG. 2). The group receiving azathioprine (a precursor of 6-MP) combined with prednisolone was 42% (5/12) MAP DNA+, compared to the group with azathioprine without prednisolone that were 10.5% (4/38) MAP DNA+ ($p<0.03$) (FIG. 3). Moreover, MAP DNA prevalence varied by geographical location and showed a correlation with disease activity and pattern of treatment ($p<0.001$) (FIGS. 4 and 5).

Given that healthy blood donors showed a significantly higher frequency of bacteria than IBD patients, thereby providing a source of disease transmission via blood transfusion, the present invention provides a method for determining whether a blood sample is suitable for transfusion by determining the presence of a MAP nucleic acid in a sample of blood prior to transfusion. In some embodiments, the nucleic acid is DNA. In so far as viability of the MAP can be determined based upon the presence of RNA, other embodiments provide that the nucleic acid is RNA. In accordance with this method, the presence of a MAP nucleic acid indicates that the blood sample is not suitable for transfusion and may be source for MAP transmission.

Detection of a MAP nucleic acid generally involves the isolation of all (e.g., RNA and DNA) or a portion (i.e., RNA or DNA) of the total nucleic acids from a sample. Such methods are well-known to those of skill in the art. For example, methods of isolation and purification of nucleic acids are described in detail in Chapter 3 of *Laboratory Techniques in Biochemistry and Molecular Biology: Hybridization with Nucleic Acid Probes*, Part I. Theory and Nucleic Acid Preparation, P. Tijssen, ed. Elsevier, N.Y. (1993).

In the detection of MAP-specific RNA molecules, total RNA can be isolated from a given blood sample using, for example, an acid guanidinium-phenol-chloroform extraction method. See, e.g., Gilberts, et al. (1994) *Proc. Natl. Acad. Sci. USA* 91:12721-12724. Frequently, it is desirable to amplify the nucleic acid sample prior to detection. One of skill in the art will appreciate that methods of amplifying nucleic acids are well-known in the art. Such suitable amplification methods include, but are not limited to polymerase chain reaction (PCR) (Innis, et al. (1990) *PCR Protocols. A guide to Methods and Application.* Academic Press, Inc., San Diego), ligase chain reaction (LCR) (see Wu and Wallace (1989) *Genomics* 4:560; Landegren, et al. (1988) *Science* 241:1077; Barringer, et al. (1990) *Gene* 89:117), transcription amplification (Kwoh, et al. (1989) *Proc. Natl. Acad. Sci. USA* 86:1173), and self-sustained sequence replication (Guatelli, et al. (1990) *Proc. Nat. Acad. Sci. USA* 87:1874).

In certain embodiments, the sample RNA is reverse transcribed with a reverse transcriptase and primers such as a collection of random oligonucleotides is used to generate a single-stranded DNA template. The second DNA strand is polymerized using a DNA polymerase. Second strand DNA synthesis can be specific or non-specific, i.e., the second strand can be synthesized with using one or more oligonucleotides which specifically hybridize to a particular MAP nucleic acid molecule. For example, MAP-specific insertion sequence, IS 900, can be amplified using primers 5'-GAA GGG TGT TCG GGG CCG TCG CTT AGG-3' (SEQ ID NO:1) and 5'-GGC GTT GAG GTC GAT CGC CCA CGT GAC-3' (SEQ ID NO:2). See, e.g., Mishina, et al. (1996) *Proc. Natl. Acad. Sci. USA* 93(18):9816 and Millar, et al. (1996) *Appl. Env. Microbiol.* 62:3446-3452. Successive rounds of transcription from each single cDNA template results in amplified RNA. Methods of in vitro polymerization are well-known to those of skill in the art (see, e.g., Sambrook, supra).

As indicated, detection of MAP nucleic acid molecules (i.e., directly or after amplification) can be achieved using a variety of established methods or combinations of methods including, e.g., northern blot analysis (see, e.g., Sambrook and Russell (2001) supra); oligonucleotide or cDNA fragment hybridization wherein the oligonucleotide or cDNA is configured in an array on a chip or wafer; RNase protection analysis; or RT-PCR, as illustrated herein. Depending on the format, detection can be performed by visual means (e.g., ethidium bromide staining of a gel). Alternatively, detection can involve indirect identification of the product via chemiluminescence, radiolabel or fluorescent label or even via a system using electrical or thermal impulse signals (Bellus (1994) *J. Macromol. Sci. Pure Appl. Chem.* A311:1355-1376). In accordance with the instant diagnostic method, the presence of a MAP nucleic acid molecule in a blood sample is indicative of the presence of MAP, and therefore transmission of a MAP-associated disease such as IBD, Multiple Sclerosis or Alzheimer's Disease.

Having demonstrated that IBD treatment with anti-MAP therapeutic agents is associated with lowered frequencies of bacteremia, the present invention also provides a method for monitoring the efficacy of an anti-MAP therapy by determining the presence or amount of a MAP nucleic acid in a sample from a patient receiving the anti-MAP therapy. In accordance with this method of the invention, the sample need not be restricted to blood and can include other fluids or tissues such as a stool sample, cerebrospinal fluid or alternatively a biopsy sample, e.g., lesioned central nervous tissue or a biopsy obtained in endoscopy. In accordance with this method, the presence or amount of a MAP nucleic acid (e.g., DNA or RNA) can be determined as described herein or using any other suitable method.

In so far as the MAP infection being treated is associated with an inflammatory bowel disease (IBD), Multiple Sclerosis or Alzheimer's Disease, treatment will also improve or ameliorate at least one sign or symptom of the IBD, Multiple Sclerosis or Alzheimer's Disease or the maintenance of disease remission. Therefore, the present invention also relates to monitoring the efficacy of a therapeutic agent used in the treatment of IBD, Multiple Sclerosis or Alzheimer's Disease.

While some embodiments of the present invention embrace directly detecting a MAP nucleic acid molecule without manipulation of the sample, other embodiments embrace isolating the nucleic acid molecule from a sample which as been cultured for an appropriate amount of time in vitro. In vitro culturing of MAP bacterium from a sample (e.g., blood sample, lesioned tissue or cerebrospinal fluid) involves placing the sample on an appropriate growth medium under suitable conditions to obtain the cell wall containing form of MAP. Such suitable conditions are known in the art and include the commercially available Mycobacteria Growth Indicator Tube (MIGT) system (Becton-Dickerson) which is an automated system containing a rich growth medium for growing MAP. To obtain a sufficient amount of MAP, the MAP can be grown for one, two, three or more months.

What is claimed is:

1. A method for determining whether a blood sample is suitable for transfusion comprising determining the presence of a *Mycobacterium avium* subspecies paratuberculosis (MAP) nucleic acid, wherein the presence of a MAP nucleic acid indicates that the blood sample is not suitable for transfusion.

* * * * *

```
SEQUENCE LISTING

<160> NUMBER OF SEQ ID NOS: 2

<210> SEQ ID NO 1
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 1
gaagggtgtt cggggccgtc gcttagg                                    27

<210> SEQ ID NO 2
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 2
ggcgttgagg tcgatcgccc acgtgac                                    27
```